United States Patent [19]
McClure et al.

[11] 4,279,346
[45] Jul. 21, 1981

[54] ASYNCHRONOUS BLUEBERRY SORTER

[75] Inventors: William F. McClure; Roger P. Rohrbach, both of Raleigh, N.C.

[73] Assignee: Southeastern Blueberry Council, Inc., Goldsboro, N.C.

[21] Appl. No.: 968,768

[22] Filed: Dec. 12, 1978

[51] Int. Cl.$^3$ ............................................. B07C 5/342
[52] U.S. Cl. ..................................... 209/582; 209/580; 209/588; 209/923; 250/223 R; 198/688
[58] Field of Search ............... 209/555, 558, 563, 564, 209/576, 580, 581, 582, 588, 629, 631, 644, 912, 922, 923; 250/223 R, 226; 198/688, 689, 698, 699, 715, 793, 844, 846

[56] References Cited

U.S. PATENT DOCUMENTS

| | | | |
|---|---|---|---|
| Re. 29,031 | 11/1976 | Irving et al. | 209/564 |
| 3,327,850 | 6/1967 | Simmons | 209/644 X |
| 3,349,905 | 10/1967 | Crawford | 209/923 X |
| 3,352,404 | 11/1967 | Settembrini | 198/689 X |
| 3,770,111 | 11/1973 | Greenwood et al. | 209/923 X |
| 3,773,172 | 11/1973 | McClure et al. | 209/580 X |
| 3,975,262 | 8/1976 | Sherwood | 209/580 X |
| 3,980,180 | 9/1976 | Jamieson | 209/912 X |
| 4,091,931 | 5/1978 | Button et al. | 209/580 X |
| 4,143,770 | 3/1979 | Grimmell et al. | 209/580 X |

FOREIGN PATENT DOCUMENTS

| | | | |
|---|---|---|---|
| 2421623 | 11/1975 | Fed. Rep. of Germany | 198/688 |
| 2509458 | 9/1976 | Fed. Rep. of Germany | 209/580 |

Primary Examiner—Robert J. Spar
Assistant Examiner—Edward M. Wacyra

[57] ABSTRACT

The present invention relates to a high speed asynchronous fruit sorter for sorting various types of fruits, such as blueberries, according to maturity. Forming a part of the fruit sorter is an open wire type conveyor having a generally M-shaped profile extending transversely across so as to define a series of laterally spaced and longitudinally extending conveying channels. An illumination source is disposed below the conveyor about an area referred to as a sorting zone. Disposed over the conveyor in the vicinity of the sorting zone is an optical maturity sensing device that continuously derives a differential optical density reading for the underlying passing fruit, and this differential optical density reading is directly related to the maturity of the fruit and is directed to a maturity discriminator circuit. The maturity discriminator circuit is in turn coupled to an air injection sorting apparatus by a series of AND gates. An optical asynchronous detector apparatus is positioned about the sorting zone and is adapted to detect the leading edge of oncoming articles of fruit and to actuate the AND gates at a selected time after detection in order that the air ejection system can be appropriately actuated to transfer certain maturity level grades to an adjacent area for receiving that particular maturity grade.

12 Claims, 5 Drawing Figures

ASYNCHRONOUS BLUEBERRY SORTER

The present invention relates to fruit sorting and conveying systems, and more particularly to an asynchronous fruit sorting apparatus that grades aligned and randomly spaced articles of fruit, such as blueberries, into one of a selected group of maturity grades.

BACKGROUND OF INVENTION

The state of the art in blueberry sorting is best evidenced by the disclosure in U.S. Pat. No. 3,773,172 to William Fred McClure et al. In that disclosure a synchronous blueberry sorter is shown. By synchronous one means that the sorter positively singulates and then advances each singulated blueberry to a read station in a definite time relationship. In the McClure et al sorter, cups are utilized to pick-up individual blueberries and the cups are carried by a conveyor means which advances them to a read station where a fiber optical type maturity sensing device is utilized to determine a differential optical density and hence the maturity of each respective blueberry. While the McClure et al synchronous blueberry sorter represented a very significant step in the art, it is evident that the limitations due to the synchronous nature of the sorter significantly limits the capacity and efficiency of the sorter. In particular, the fact that the conveyor itself has to be driven at a relatively slow speed that enables the blueberries to be picked up by the respective cups inherently limits the speed of the conveyor and cups, and consequently the capacity of the sorter. In addition, the cup design limits the density of the blueberries being fed to the read station because the blueberries can only be advanced to the read station by the cups themselves. The importance of high capacity and efficiency cannot, as a practical matter, be overemphasized because commercially available blueberry harvesters and associated packaging and processing equipment have relatively large capacities and it is desirable for the capacity of the sorter to be comparable.

SUMMARY OF INVENTION

The present invention relates to an asynchronous high speed fruit or blueberry sorter that, as compared to the McClure et al synchronous blueberry sorter, has a greatly increased sorting capacity. As a part of the asynchronous high speed blueberry sorter of the present invention, there is provided a wire type conveyor having a generally M-shaped transverse profile that defines a series of laterally spaced and longitudinally extending conveying channels. Certain conveying channels are designated input conveying channels and are adapted to convey aligned but randomly spaced blueberries past a sorting zone. As the blueberries are fed to and through the sorting zone, a differential optical density reading is made and this is a measure of maturity of the underlying passing blueberries. An asynchronous position detection device is utilized to sense the position of oncoming blueberries and to effectively cause the actuation of an associated air jet sorting system that transfers selected blueberries according to maturity from the input channel to one or more adjacent conveying channels designated a particular maturity grade. Thus, each blueberry is subjected to a maturity determination and the position detection device is operative to cause respective blueberries to be transferred from the input channel to another channel if their determined maturity is other than the designated maturity for blueberries preceding from the sorting zone in the input channel.

It is, therefore, an object of the present invention to provide an asynchronous fruit sorter that sorts according to maturity and which substantially increases sorting capacity over conventional synchronous fruit sorters.

A further object of the present invention resides in the provision of a high speed asynchronous blueberry sorter that is capable of sorting fruit into multiple maturity categories or grades with accuracy and precision.

A very important object of the present invention resides in the provision of a high speed asynchronous fruit sorter provided with a fiber optic maturity sensing and determining apparatus and a conveyor that does not significantly affect differential optical density readings, thereby enabling the asynchronous fruit sorter to make maturity determinations independently of the conveyor or the position thereof.

Still a further object of the present invention is to provide a high speed asynchronous fruit sorter with a sorting conveyor that is capable of producing a highly precise three-way maturity sort within a relatively short run of the conveyor.

A further object of the present invention is to provide a high speed asynchronous fruit sorter of the character described above wherein the sorter is provided with a conveyor having at least one longitudinally extending fruit carrier channel having elevated side retaining means about each side thereof for advancing aligned but randomly distributed articles of fruit to a sorting zone, where a multiple maturity sort may take place and cause selected articles of fruit to be transferred from the defined carrying channel over the side retaining means thereof and directed to an appropriate adjacent area with other like maturity grades.

A further object of the present invention is to provide an asynchronous fruit sorter where the portion of the fruit and its optical sorting parameter are sensed as the fruits flow randomly through the system.

It is also an object of the present invention to provide a high speed asynchronous fruit sorter that minimizes damage and bruising of the fruit in the course of the fruit being transferred to respective areas during the sorting process.

A further object of the present invention is to provide a high speed asynchronous fruit sorter having multiple input channels with each input channel being directed to a particular sorting zone.

Another object of the present invention is to provide a high speed asynchronous fruit sorter that is particularly adapted to efficiently discharge the fruit after sorting by conveying the separated multigraded fruit from the sorting zone in side-by-side relationship about a multi-channel generally M-shaped conveyor.

Other objects and advantages of the present invention will become apparent from a study of the following description and the accompanying drawings which are merely illustrative of the present invention.

DESCRIPTION OF PREFERRED EMBODIMENT

Figure 1:
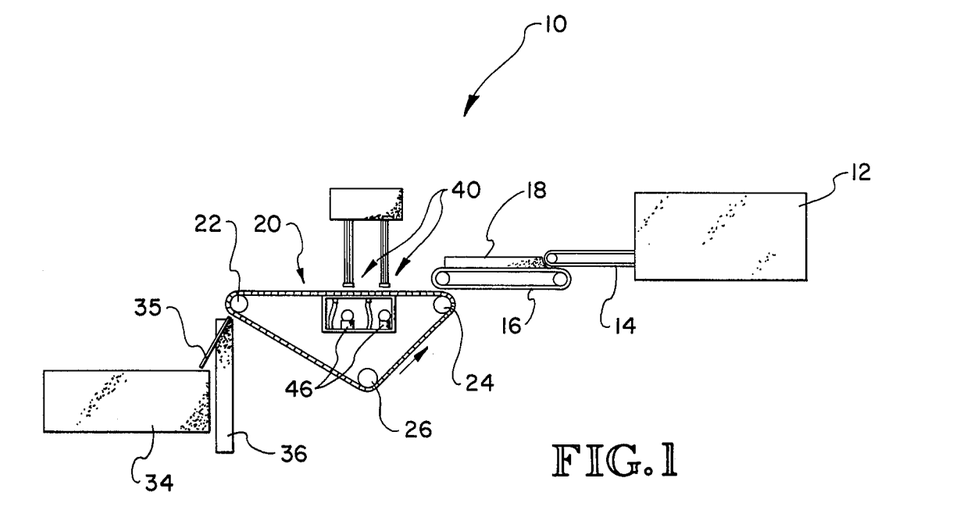
FIG. 1 is a schematic illustration of the high speed asynchronous fruit sorter of the present invention.

With further reference to the drawings, particularly FIG. 1, the asynchronous fruit sorter of the present invention is illustrated therein and indicated generally by the numeral 10. Throughout the following specification, the asynchronous fruit sorter 10 will be referred to as a blueberry sorter since it was primarily designed to sort blueberries. However, the basic features and design characteristics of the asynchronous sorter 10 permit the same to be utilized in sorting other fruits such as cranberries, oranges, apples, grapes, cherries, and any other fruit or vegetable.

Referring to the schematic illustration of FIG. 1, a hopper 12 is provided to contain the blueberries or other fruit to be sorted. In order to transfer the blueberries from the hopper 12, it is contemplated that a series of infeed conveyors would be utilized, with each succeeding conveyor being adapted to convey the blueberries from one conveyor to another. It will be appreciated that this enables the infeed conveying system to feed the article of fruit at a relatively high speed and yet assures that the layer of blueberries finally reaching the sorting mechanism is only one blueberry deep. As illustrated in FIG. 1, there is provided two infeed conveyors, conveyor 14 and conveyor 16. Conveyor 16 includes a shield 18 having a transverse inverted V-shaped profile that is designated such that the blueberries exiting conveyor 16 are discharged in laterally spaced rows so as to conform with the basic design principles of the sorter 10. The purpose of the shield 18 will be more fully understood from subsequent portions of this disclosure.

Disposed adjacent the discharge end of conveyor 16 is a driven sorting conveyor, indicated generally by the numeral 20. Conveyor 20 is an endless conveyor that is trained around idlers 22 and 24, and driven by sprocket 26 counterclockwise as viewed in FIG. 1. The sorting conveyor 20 is referred to as a M-belt conveyor since the same includes a generally M-shaped profile that extends transversely across the conveyor, as partially illustrated in FIG. 2. The M-belt 20 is basically comprised of a single knit stainless steel wire belt that in a preferred embodiment includes 1.27 mm Dia. wire with a 7 mm pitch.

Figure 2:
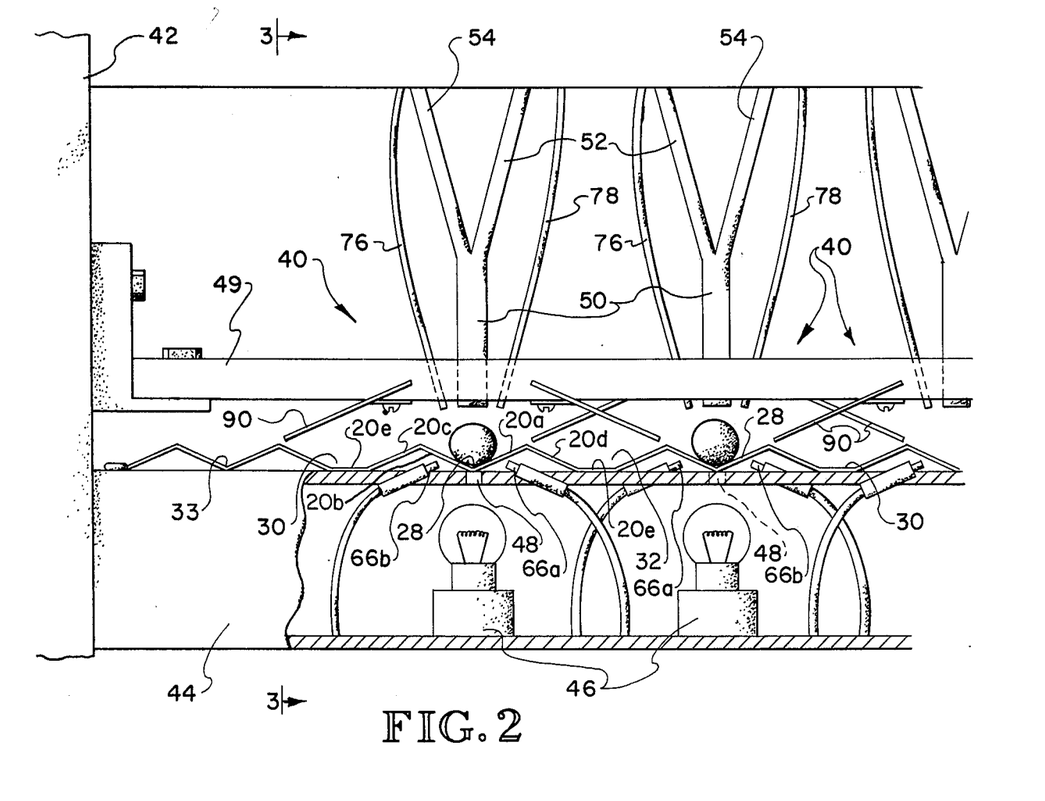
FIG. 2 is a fragmentary transverse sectional view of a portion of the fruit sorter of the present invention particularly illustrating the generally M-shaped conveyor and a series of transversely spaced sorting stations or zones.
Figure 3:
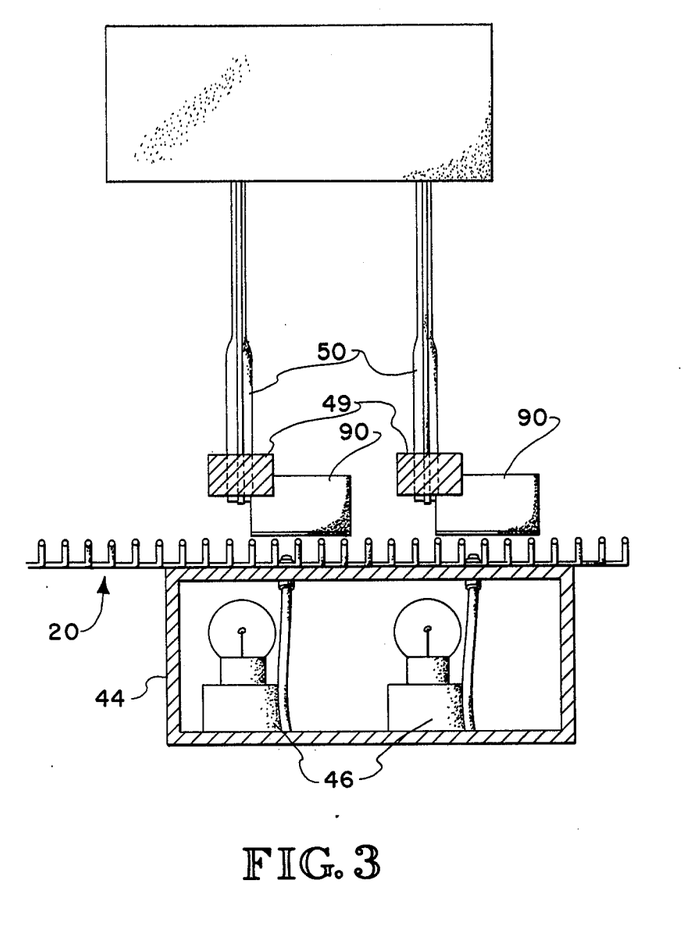
FIG. 3 is a sectional view taken along the lines 3—3 of FIG. 2.

Referring to a typical M section of the M-belt conveyor 20, it is seen that the same includes two laterally spaced side retaining means 20a and 20b that extend upwardly to form a V-shaped input channel. Extending downwardly from the side retaining means 20a and 20b is a pair of outer legs 20c and 20d. The end extremities of the M-section include a section denoted by 20e that extends outwardly from the lower terminal end of legs 20c and 20d. As seen in FIG. 2, this typical M section design occurs successively transversely across the entire M-belt conveyor 20.

In forming the M-belt 20, a flat configuration of the single knit stainless steel wire mesh can be utilized. In a preferred embodiment, the flat configuration wire mesh can be cut into sections having an approximate width of 25 centimeters, and with the use of a continuously-progressive die respective "M" profiles can be pressed sequentially across the cut sections of the wire mesh. Once the pressed sections are joined together to form the endless M-belt 20, the belt of this embodiment will include five separate input channels 28 with each respective input channel having an overripe channel 30 and an underripe (green) channel 32 to each side thereof, as partially illustrated in FIG. 2. A dummy channel 33 is formed along each longitudinal edge of the fabricated M-belt 20.

As will be evident from subsequent portions of this disclosure, the actual maturity sensing and maturity determination, and sorting will occur between the receiving and discharge ends of the M-belt conveyor 20. The adjacent infeed conveyor 16 is preferably of a like M-belt design, and because of the particular M-shaped design and spacing of the shield structure 18, blueberries received by conveyor 16 are received in channels on the conveyor 16 that are aligned with the input channels 28 of the M-belt sorting conveyor 20. The basic sorting scheme of the asynchronous fruit sorter 10 of the present invention involves making a maturity determination of each blueberry directed to a sorting zone on the M-belt conveyor 20. In making the maturity determination, the asynchronous fruit sorter 10 of the present invention is designed to determine if the blueberry is ripe, overripe or underripe. According to this maturity determination and sorting scheme, if the blueberry is ripe, it is allowed to continue to pass through the sorting zone in the input channel 28 which can then be appropriately referred to as the output ripe channel once the blueberry has passed the sorting zone. If the blueberry is overripe or underripe, then by the use of timed control air ejection blasts the respective overripe and underripe blueberries are transferred from the input channel 28 to either the adjacent overripe channel 30 or the adjacent underripe channel 32.

Disposed adjacent the discharge end of the M-belt 20 is a receptacle 34 for receiving the ripe blueberries. Extending between the discharge end of the M-belt conveyor 20 and the receptacle 34, is a series of guide plates 35 that are aligned with the input/ripe channels 28 for directing the ripe blueberries from these respective channels downwardly into the receptacle 34. Intermediately spaced between the guides 35 is a series of over and underripe manifold inlet openings 36 that are disposed directly underneath the discharge end of the M-belt conveyor 20 in alignment with the over and underripe channels 30 and 32 for receiving over and underripe blueberries and directing them to a collecting area (not shown).

THE ASYNCHRONOUS SORTING SYSTEM

For each input channel 28, there is provided a sorting zone or area, indicated generally by the numeral 40, intermediately between the receiving and discharge ends of the M-belt conveyor. It is at these sorting zones where the maturity of each respective blueberry is determined and where sorting between ripe, overripe and underripe maturity stages takes place.

As basically shown in FIG. 2, a main frame structure 42 supports the M-belt conveyor 20 by supporting housing structure 44 that extends transversely below the M-belt conveyor 20 in the vicinity of the sorting zones 40. Particularly provided in the housing structure 44 is an illumination source 46 for each sorting zone, with the illumination source being disposed within the housing structure 44 beneath an aperture 48 formed within the top of the housing structure 44. It is appreciated that each illumination source is directly aligned with a respective input channel 28. A fan (not shown) is used to cool the housing structure containing the illumination sources.

In the McClure et al disclosure, U.S. Pat. No. 3,773,172, it is disclosed that the maturity of blueberries can be determined by determining the difference in optical density at two wavelengths. In particular, it is known that the maturity of the berries is proportional to the difference in optical density of the berries at 740 nanometers and the optical density at 800 nanometers. Details of this maturity determination is not dealt with herein in detail because such is known in the art. But for a more detail and complete understanding of the basics involved, one is referred to the disclosure of McClure et al in U.S. Pat. No. 3,773,172, the disclosure of which is expressly incorporated herein by reference.

But briefly discussing this method of maturity sensing, a fiber optical bundle 50 is mounted above each light source 46 in the respective sorting zone 40. The fiber optic bundle 50, as illustrated in FIG. 2, is supported by a cross member 49 that extends transversely between the main frame structure 42 of the fruit sorter 10. Each fiber optic bundle 50 includes bifurcated branches 52 and 54, each of which lead to a particular filter element and a photomultiplier tube. As shown in FIG. 8 of the McClure et al disclosure, the output signal of each photomultiplier tube for the two particular wavelengths involved are directed to a logarithmic amplifier, from which the output of the logarithmic amplifiers is directed to a difference amplifier whose output is directly proportional to the difference in optical density of the article of fruit being measured at the two particular wavelengths measured. Therefore, the maturity of the respective blueberries can be said to be related to and proportional to the output signal of the difference amplifier.

Figure 5:
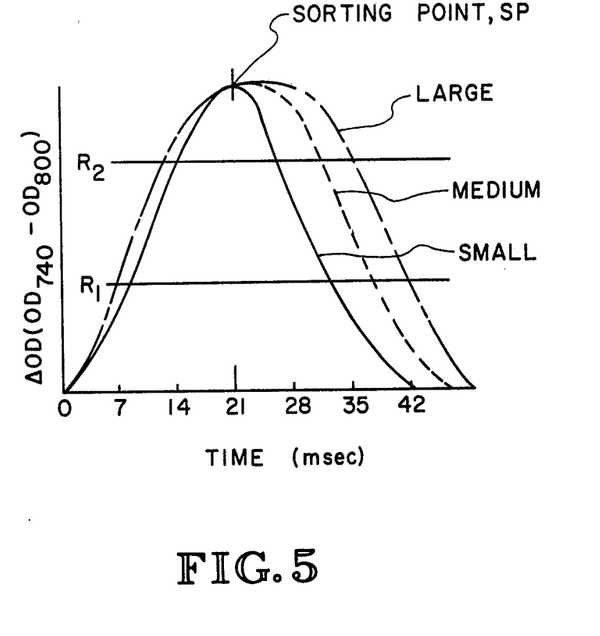
FIG. 5 is a graphic illustration of a series of differential optical density curves, plotted with respect to time, for three different size fruits.

With reference to FIG. 5, it can be determined that a differential optical density less than a selected first reference $R_1$ would be an indication of green or underripe maturity, while an optical density difference greater than a second reference line $R_2$ would indicate an overripe berry. An optical density equal to or lying between the reference lines $R_1$ and $R_2$ would indicate a ripe berry. Such reference levels can be experimentatively established. Furthermore, in FIG. 5, it should be noted that time equal to zero occurs when the differential optical density measurement circuit first responds to the oncoming berry.

Figure 4:
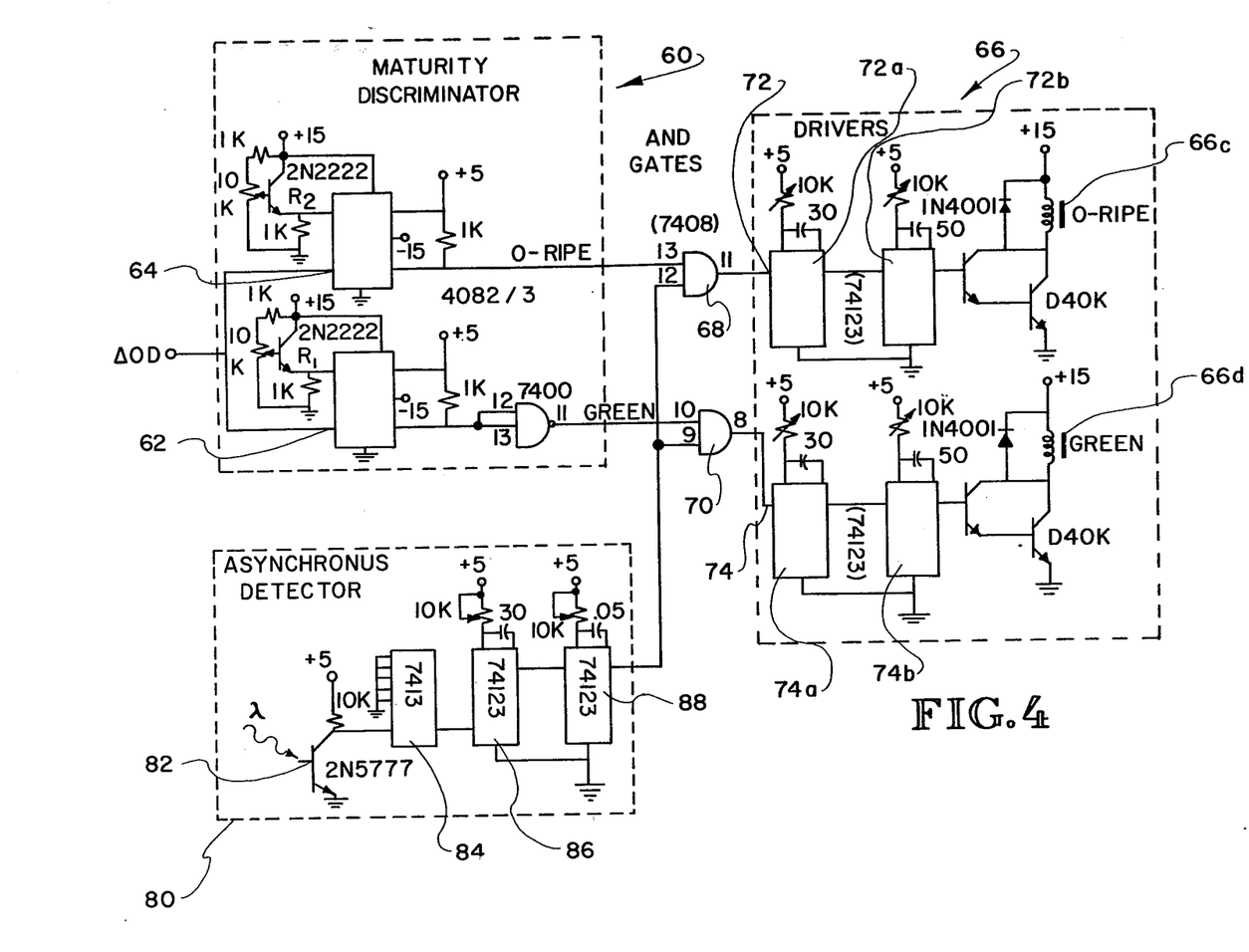
FIG. 4 is a schematic illustration of the maturity discriminator, asynchronous detector, and driver or air jet ejection control circuit that form a part of the sorting control system of the asynchronous fruit sorter of the present invention.

Therefore, it is appreciated that as each blueberry or fruit passes underneath the respective fiber bundle 50, a differential optical density pulse is generated and the magnitude of this pulse is proportional to the maturity of the blueberry. This optical density difference signal, referred to as $\Delta OD$ is then directed to a maturity discriminator circuit 60, as shown in FIG. 4, that includes two analog comparators 62 and 64 that continuously monitor the level of the incoming $\Delta OD$ signal. The $\Delta OD$ reference input signal into the comparator 62 and 64 is controlled by a 2N2222 transistor hooked in the emitter-follower configuration to reduce the output impedance of the 10 K potentiometer. Without this transistor, the comparators would shift the level of the reference signal when the comparators toggle, thereby causing oscillation or error in the detection level.

Comparator 62 is referred to as the green/ripe comparator in that the same is designed such that the output thereof is high if the incoming $\Delta OD$ signal does not exceed the reference setting $R_1$ (FIG. 5), indicating the presence of a green or underripe berry or fruit. Comparator 64, on the other hand, is referred to as the overripe/ripe discriminator since the same is designed such that it has a high output if the incoming $\Delta OD$ signal exceeds the reference level $R_2$, indicating on through the sorting zone 40 in the output ripe channel 28. Consequently, it is the function of the maturity discriminator 60 to identify the green and overripe berries, and it follows that all other berries would be deemed to be ripe.

To transfer and to effectuate sorting at each sorting zone, there is provided a pair of air ejectors disposed below the M-belt conveyor 20 generally adjacent the respective input channels 28 thereof, as illustrated in FIG. 2. The pair of air ejectors at each sorting station, includes an overripe ejector 66a and an underripe or green ejector 66b, with each ejector being adapted to release an air blast towards a particular blueberry disposed in the input channel and to cause the same blueberry to be elevated and transferred over the side retaining means 20a and 20b of the input channel and to fall in an adjacent overripe or underripe channel 30 or 32.

Cooperating with each the air ejectors 66a and 66b is a deflector 90 that is disposed over the M-belt conveyor 20 and opposite the respective ejector. The deflector 90 assures that a blueberry or article of fruit ejected from the input channel 28 is deflected back down into an adjacent underripe or overripe channel 30 or 32 disposed below the deflector 90.

Each of the underripe and overripe air ejectors 66a and 66b are connected to a source of air and are controlled by a driver control system indicated generally by the numeral 66 in FIG. 4. More particularly, the analog comparators 62 and 64 of the maturity discriminator circuit 60 are coupled to the air ejector control system 66 through a pair of AND gates 68 and 70.

Thus for each blueberry passing through the sorting zone 40, there is produced a $\Delta OD$ pulse that is directed to the maturity discriminator circuit 60, and the maturity discriminator circuit 60 is in turn coupled to the air ejector or driver control circuit 66 that includes an overripe actuating circuit 72 and an underripe actuating circuit 74 that is adapted to actuate the respective over and underripe air ejector 66a and 66b. To effectuate the transfer of over and underripe berries from the input channel 28 to appropriate over and underripe channels 30 and 32, it is required that the asynchronous fruit sorter 10 of the present invention be provided with some control means for detecting the position of each berry passing through the sorting zone and to in turn actuate the AND gates 68 and 70 at a time that is calculated for the respective berry of concern to be properly aligned with the respective air ejector 66a and 66b for effectuating the transfer.

To accomplish this, an asynchronous detector apparatus is utilized, and includes two optical wave guides 76 and 78 which are mounted above the illumination source 46 as shown in FIG. 2. The optical wave guides 76 and 78 are transversely spaced and are radially directed towards the aperture 48 above the light source through which the light beams from the illumination source 46 are upwardly directed.

With reference to FIG. 4, there is shown an asynchronous detector control circuit, indicated generally by the numeral 80, that includes a phototransistor 82 which is disposed to receive light from either of the optical wave guides 76 and 78. The phototransistor 82 is commerically referred to as a 2N5777 phototransistor, and in the asynchronous detector circuit 80 is connected to a 7413 Schmidt trigger circuit 84. The phototransistor 82 is adapted to operate in two basic states, one being referred to as a non-conductive state and the other being referred to as a conductive state. Generally the phototransistor 82 is maintained in a conductive state when either or both of the optical wave guides 76 and 78 sees light, which in effect means the absence of an article of fruit between the respective optical wave guides 76 and 78 and the light source 46. To detect the leading edge of an article of fruit, both optical wave guides must sense less light (i.e. become relatively dark). This causes the phototransistor 82 to change from its conductive state to a nonconductive state, and to effectively actuate the Schmidt trigger circuit 84. The pulse produced by the Schmidt trigger circuit 84 than activate a first one shot 86 which is adapted to generate a short pulse that is a fixed interval of time delay of time from the general point of entry of the berry into the detection beam until it is desired to initiate the air blast. The short pulse generated by one shot 86 is then directed to a second one shot 88 which produces a "read" pulse which is directed to the AND gates 68 and 70.

It is important that the berry or fruit move to a sorting point SP, a point defined where ΔOD peak is a maximum, before the ΔOD pulse is evaluated. The one shot 86 of the asynchronous detector circuit 80 provides for this delay, since the berries edge is what is first detected and not the center of the berry.

FIG. 5 illustrates ΔOD profiles for three different size berries with the same pigment concentration. The three curves are generally synchronous about the leading edge as it takes approximately 21 ms for the fruit to travel from the leading edge to the sorting point SP. This was established with the fruit flowing at approximately 50 CM/S. From this, it is concluded that the time required to reach maximum ΔOD is about the same for the three different size berries. Consequently for best results, the system should be calibrated and adjusted to read the smaller fruit, since the error in reading larger fruit will be minimized.

Therefore, the position of the overripe and underripe ejectors 66a and 66b for each sorting zone 40 is determined as they are particularly positioned with respect to the fiber optic bundles 50 such that the read pulse directed to the AND gates 68 and 70 occur simultaneously with the center of the berry being aligned with the mid-point in timing of air blast from the respective ejectors 66a and 66b.

Viewing the driver control circuit 66 in more detail, control circuits 72 and 74 are operative to actuate separate control valves, schematically indicated at 66c and 66d. Control valves 66c and 66d are operatively connected between an air source (not shown) and air jet nozzles 66a and 66b. In addition, each control circuit 72 and 74 is shown to include two one-shot delay circuit means 72a, 72b, 74a and 74b connected in series. Generally this delay resulting from the one-shot 88 in the asynchronous control circuit 80 is sufficient for effective operation of the air jet nozzles 66a and 66b. Consequently one shots 72a, 72b, 74a, and 74b may not be necessary in some applications. However, where the speed of the M-belt conveyor 20 is relatively fast, it may be desirable to include one or both of the one shots in both circuits 72 and 74 to control the duration of the air blast and/or the critical time where the center line of each article of fruit aligns with the center line of the nozzles' air blast.

In the preferred embodiment with five input channels 28, a sorting zone 40 would be provided for each input channel and the sorting zones would preferably be transversely staggered to avoid in-flight collision of fruit being transferred to over and underripe channels 30 and 32. Briefly reviewing the basic sorting system at each sorting zone, it is appreciated that in accordance with the preceding discussion that at each sorting zone a source of illumination is provided beneath the M-belt conveyor 20, along with an optical fiber bundle 50 and associated apparatus for determining the differential optical density of each article of fruit passing thereunder. As discussed hereinbefore, the differential optical density at two selected wavelengths is directly related to the maturity of the articles of fruit. The differential optical density signal, referred to as ΔOD, is directed to a maturity discriminator circuit 60 having a series of comparator circuits that evaluate the incoming differential optical density signal. The respective comparator circuits are referred to as a ripe/overripe discriminator, a ripe/underripe or green discriminator, etc. A logic network made up of AND and NAND gates is interconnected between the comparator circuits and a driver control circuit 66. The ripe/overripe comparator circuit 64 is operatively connected to AND gate 68 that couples the same with ejector control circuit 72. Likewise, the ripe/underripe comparator circuit 62 is operatively connected to AND gate 70 which in turn is connected to the ejector control circuit 74 of the driver control system 66 that is operative to actuate the control valve that controls the green or underripe air ejection nozzle 66b at each sorting zone.

To control the time at which the comparator circuits 64 and 62 actually evaluate an incoming differential optical density signal and ultimately control the time at which the respective air ejection nozzles 66a and 66b are actuated, there is provided an asynchronous detector apparatus for detecting the leading edge of oncoming articles of fruit and which produces a "read" output signal that is directed to the AND gates 68 and 70. This "read" output signal is operative such that the AND gate coupled to the comparator circuit having the relatively high output voltage is closed and a respective air ejector 66a or 66b may be actuated to cause either an underripe or overripe article of fruit to be blown from a particular input channel 28 to either an overripe or underripe channel 30 or 32.

It is contemplated that the M-belt conveyor 20 could be driven at a speed as great as two meters per second, which in a design having five input channels could theoretically accommodate a sorting capacity of approximately 450 kg/hr.

The terms "upper", "lower", "forward", "rearward", etc., have been used herein merely for the convenience of the foregoing specification and in the appended claims to describe the asynchronous blueberry sorter and its parts as oriented in the drawings. It is to be understood, however, that these terms are in no way limiting to the invention since the asynchronous blueberry sorter may obviously be disposed in many different positions when in actual use.

The present invention, of course, may be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended Claims are intended to be embraced therein.

What is claimed is:

1. A high speed asynchronous fruit sorting apparatus for sorting aligned and randomly spaced articles of fruit according to maturity, comprising: a driven sorting conveyor assembly having a receiving end and a discharge end and comprising a generally open mesh type conveyor having a plurality of generally M-shaped profiles extending transversely across the conveyor so as to define a plurality of laterally spaced and longitudinally extending fruit receiving and selected maturity channels about the conveyor; at least one maturity sorting zone disposed adjacent said conveyor intermediately between said receiving and discharge ends of said conveyor and including a source of illumination disposed below said conveyor for illuminating the passing articles of fruit; said maturity sorting zone including maturity sensing means for effectively determining the maturity of respective articles of fruit conveyed to said maturity sorting zone independently of said conveyor, said maturity sensing means including fiber optic means for capturing light rays diffused by the articles of fruit and means operatively associated with said fiber optic means for generating differential optical density signals based on the transmittance of the respective articles of fruit at two selected wavelengths, whereby the magnitude of the produced differential optical density signal is related to maturity; an air ejection apparatus having at least two air jet nozzles disposed about each sorting zone and including a control circuit for actuating selected individual air jet nozzles; a maturity discriminator circuit operatively connected to the control circuit of said air ejection apparatus and adapted to receive said differential optical density signals and to effectively evaluate the signals to determine the maturity state of respective articles of fruit; and an asynchronous position detector apparatus disposed about each sorting zone for detecting oncoming articles of fruit and including an actuating control circuit responsive to the detection of oncoming articles of fruit for effectively actuating the maturity discriminator circuit so as to evaluate a certain differential optical density signal representative of a selected article of fruit at an appropriate time in order that the same may effectively actuate the control circuit of said air ejection apparatus such that either of said air ejector nozzles may be actuated in order to effectuate the transfer by air of an article of fruit to an appropriate adjacent channel on the M-shaped conveyor designated to receive that particular maturity grade.

2. The asynchronous sorting apparatus of claim 1 wherein said asynchronous position detector apparatus for detecting the position of respective oncoming articles of fruit includes a pair of optical wave guides that are laterally spaced relative to the line of oncoming fruit in said input channel and wherein said optical wave guides are particularly positioned above said M-shaped conveyor such that either is effective to sense light being directed thereto by said source of illumination; and wherein said control circuit of said asynchronous detector apparatus includes photosensitive actuating means for generating an output signal in response to the detection of the leading edge of an article of fruit by said optical wave guides; a trigger circuit operatively connected to said photosensitive actuating means and actuated by an output signal thereof; and one shot delay circuit means operatively connected to said trigger circuit for delaying the output signal of said asynchronous control circuit a predetermined length of time in order that the respective articles of fruit may be appropriately positioned within the sorting zone before maturity readings are evaluated and sorting occurs.

3. The asynchronous sorting apparatus of claim 2 wherein AND gate control means is operatively interconnected between said maturity discriminator circuit and said control circuit for said air ejection apparatus; and wherein the output of said asynchronous detection circuit is operatively connected to said AND gate control means for actuating the same in response to the detection of the position of respective articles of fruit passing through said sorting zone.

4. The asynchronous fruit sorter of claim 3 wherein said maturity discriminator circuit includes at least two comparator circuit means for receiving input differential optical density signals for respective articles of fruit and producing an output signal that is indicative of the maturity of the respective articles of fruit; and wherein the output of said maturity discriminator circuit and said comparator circuit means thereof is connected to said control circuit of said air ejection apparatus with said AND gate control means being operatively connected therebetween.

5. The asynchronous sorting apparatus of claim 3 wherein said control circuit of said air ejection apparatus includes a series of individual control circuits with each control circuit being designated as a selected maturity stage control circuit and operative to actuate a certain air jet nozzle positioned within said sorting zone to transfer respective articles of fruit of that corresponding maturity stage to a selected channel on said M-shaped conveyor designated to receive that particular maturity stage; and wherein said maturity discriminator circuit includes a like number of individual comparator circuits with each such comparator circuit being adapted to produce a relatively high output voltage signal in response to the received differential optical density signal being of a magnitude corresponding to its selected maturity range, and wherein each respective comparator circuit is connected to a corresponding maturity stage control circuit of said air ejection apparatus with a respective AND gate operatively connected therebetween, and whereby said asynchronous detector actuating control circuit is operatively connected to said plurality of AND gates such that the output "read" signal thereof is operative to effectively close the circuit between the individual comparator circuit of said maturity discriminating circuit having the relatively high output voltage and the corresponding control circuit of said air ejection apparatus in response to each "read" pulse transferred to said AND gates.

6. The high speed asynchronous fruit sorting apparatus of claim 1 including a plurality of transversely spaced maturity sorting zones with each sorting zone being disposed about a section of at least three laterally spaced fruit conveying channels defined by said M-shaped conveyor, with at least one channel being designated an input channel and certain other channels being designated to convey certain maturity grades; and wherein said air ejection apparatus is operative to transfer selected articles of fruit from said input channel to another channel of that section according to maturity.

7. A high speed asynchronous fruit sorting apparatus for sorting fruits into a plurality of maturity grades comprising: conveyor means having laterally spaced apart and generally longitudinally aligned side retaining means that are elevated so as to define at least one longitudinally extending input channel for receiving fruit products therein such that the respective fruit products received within said defined input channel are generally aligned and maintained one behind the other in random spaced apart relationship; a maturity sensing and sorting zone disposed adjacent said conveyor means and including a source of illumination disposed below said conveyor means for transmitting light through the passing articles of fruit; optical maturity sensing means situated at said sensing and sorting zone and aligned with said input channel for sensing light transmittance through said fruit and effectively determining the maturity of respective articles of fruit passing within said input channel, said maturity sensing means including fiber optic means for capturing light rays diffused by said articles of fruit and means operatively associated with said fiber optic means for generating differential optical density signals based on light transmittance of the respective articles of fruit at two selected wavelengths, whereby the magnitude of the produced differential optical density signal is related to maturity; an air ejection apparatus having at least two air jet nozzles disposed about each maturity sensing and sorting zone and disposed directly adjacent said optical maturity sensing means for blowing and transferring selected articles of fruit from said input channel over said side retaining means immediately after maturity determination and in response to the maturity of respective articles of fruit being determined such that maturity determination and grading occurs in rapid time sequence about the same area of said conveyor means, said air ejection apparatus including a control circuit for actuating selected individual air jet nozzles and wherein said air jet nozzles are directed toward said input channel and operative upon actuation to blow in an unassisted fashion certain articles of fruit upwardly from a sitting position within said input channel over the side retaining means forming a part thereof; a maturity discriminator circuit operatively connected to the control circuit of said air ejection apparatus and adapted to receive said differential optical density signals and to effectively evaluate the signals to determine the maturity state of respective articles of fruit; and an asynchronous position detector apparatus disposed about each sorting zone for detecting oncoming articles of fruit and including an actuating control circuit responsive to the detection of oncoming articles of fruit for effectively actuating the maturity discriminator circuit so as to evaluate a certain differential optical density signal representative of a selected article of fruit at an appropriate time in order that the same may effectively actuate the control circuit of said air ejection apparatus such that either of said air jet nozzles may be actuated so as to blow the selected article of fruit from said input channel upwardly and over said side retaining means.

8. The high speed asynchronous fruit sorter of claim 7 wherein said conveyor means includes a mesh type conveyor wherein the structure comprising the same is relatively optically opaque such that the presence of a portion of the conveyor beneath an article of fruit does not significantly affect the differential optical density reading thereof.

9. A sorting apparatus for sorting longitudinally aligned products such as fruits or articles in accordance to predetermined grades, comprising: a laterally extending product supporting conveyor means including laterally extending product support elements and operatively associated laterally spaced and longitudinally extending side retaining means that are elevated so as to define at least one longitudinally extending input channel for receiving products therein such that the respective products received in that defined input channel are maintained one behind the other and are at least partially supported by said laterally extending product support elements that extend transversely between said side retaining means; a sensing and sorting zone disposed adjacent said conveyor means and including a source of illumination spaced relative to said conveyor means for illuminating products conveyed within said input channel, and optical sensing means disposed adjacent said conveyor means and spaced with respect to said source of illumination for sensing the resultant light of said products and effectively determining the grade of respective products being conveyed within said input channel; said optical sensing means including means for sensing generally through the lateral product support elements that extend across said input channel between said illumination source and said optical sensing means in such a manner that the lateral support elements actually pass through the resulting optical light path existing between said illumination source and said optical sensing means; and grading means operatively associated with said sensing means and responsive thereto for effectively grading the products by causing the respective products to be transferred from said input channel to an appropriate area where the respective grades are collected.

10. The sorting apparatus of claim 9 wherein said conveyor means comprises a generally lateral M-shaped profile wherein said lateral product elements are formed into generally M-shaped lateral segments wherein from the lower central portion of the M-shaped lateral segment the respective lateral product support elements extend upwardly and outwardly to form said side retaining means and wherein said area therebetween is said input channel.

11. The sorting apparatus of claim 10 wherein said laterally extending product support elements are comprised of a series of longitudinally spaced wire type elements that form a generally open mesh type conveyor means.

12. The sorting apparatus of claim 9 wherein said sensing means and said grading means form said sensing and sorting zone, and wherein said sorting apparatus includes a plurality of sorting zones that are laterally spaced and longitudinally staggered from each other to permit laterally spaced sorting zones to transfer a common grade from their respective input channels to a selected area simultaneously.

* * * * *